United States Patent [19]

Whittemore

[11] Patent Number: 5,925,616

[45] Date of Patent: Jul. 20, 1999

[54] TREATMENT OF FUNGAL INFECTIONS USING A COMBINATION OF AN ANTI-FUNGAL COMPOUND AND AN H-ALKYL HETEROCYCLIC COMPOUND

[75] Inventor: Marilyn S. Whittemore, Memphis, Tenn.

[73] Assignee: Buckman Laboratories International, Inc., Memphis, Tenn.

[21] Appl. No.: 08/907,490

[22] Filed: Aug. 8, 1997

Related U.S. Application Data

[60] Provisional application No. 60/023,642, Aug. 9, 1996.

[51] Int. Cl.⁶ ............... A61K 38/00; A61K 31/535; A61K 31/50; A61K 31/445
[52] U.S. Cl. ............... 514/2; 514/12; 514/23; 514/231.2; 514/247; 514/315; 514/359; 514/374; 514/396; 514/408; 514/424; 514/460; 424/422
[58] Field of Search ............... 514/2, 12, 23, 514/231.2, 247, 315, 359, 374, 396, 408, 424, 460; 424/422

[56] References Cited

U.S. PATENT DOCUMENTS

| | | | |
|---|---|---|---|
| 5,229,397 | 7/1993 | Seele et al. | 514/317 |
| 5,250,194 | 10/1993 | Hollis et al. | 210/764 |

FOREIGN PATENT DOCUMENTS

| | | |
|---|---|---|
| 39 35 113 | 4/1991 | Germany . |
| 43 43 176 | 6/1995 | Germany . |
| WO 84/01102 | 3/1984 | WIPO . |
| WO 88/06841 | 9/1988 | WIPO . |
| WO 92/15286 | 9/1992 | WIPO . |
| WO 95/30417 | 11/1995 | WIPO . |

OTHER PUBLICATIONS

Firestone et al., *J. Med. Chem.*, 30(8), 1519–1521 (1987).
de Savignac et al., *Eur. J. Med. Chem.*, 25(5), 449–454 (1990).
Windholz et al, *The Merck Index*, 10th Ed. (1983) various antifungal compounds.

*Primary Examiner*—Kevin E. Weddington
*Attorney, Agent, or Firm*—Morgan, Lewis & Bockius LLP

[57] ABSTRACT

A method for increasing the effectiveness of an anti-fungal compound is described. In the method, an anti-fungal compound and an N-alkyl heterocyclic compound or a salt thereof are administered to a mammal in a combined amount effective to treat a fungal infection. The N-alkyl heterocyclic compound or salt thereof is present in an amount effective to potentiate or increase the anti-fungal activity of the anti-fungal compound. The N-alkyl heterocyclic compound has the formula:

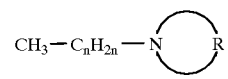

The variable "n" ranges from 5 to 17, and the heterocyclic ring defined by

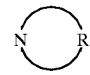

is a substituted or unsubstituted ring having four to eight members. A pharmaceutical composition is described where the anti-fungal compound and the N-alkyl heterocyclic compound or salt thereof are present in a combined amount effective to treat a fungal infection. A method for controlling the growth of fungal organisms on various substrates to be inserted into the body using a combined amount of an anti-fungal compound and an N-alkyl heterocyclic compound or a salt thereof is also described.

20 Claims, No Drawings

TREATMENT OF FUNGAL INFECTIONS USING A COMBINATION OF AN ANTI-FUNGAL COMPOUND AND AN H-ALKYL HETEROCYCLIC COMPOUND

This application claims benefit of provisional application Ser. No. 60/023,642, filed Aug. 9, 1996.

BACKGROUND OF THE INVENTION

FIELD OF INVENTION

The present invention relates to the use of an anti-fungal compound and an N-alkyl heterocyclic compound or a salt thereof to treat fungal infections in humans and animals. In the N-alkyl heterocyclic compound or salt thereof, a nitrogen is a part of the heterocyclic ring with an alkyl chain of 6–18 carbons attached to the nitrogen.

BACKGROUND

Fungal organisms, such as dermatophytes, Trichophyton, Microsporum and Epidermophyton, different Candida species, Trichoderma, Cryptococcus, Aspergillus, Zygomyetes and Fusarium, can cause infections in humans and animals. These fungal organisms are ubiquitous in air, soil, food, decaying food, etc. Histoplasmosis, Blastomyces, and Coccidioides, for example, cause lower respiratory infections. *Trichophyton rubrum* causes difficult to eradicate nail infections. *Hendersonula toruloidea* and *Scopulariopsis brevicaulis* are known to cause tinea pedis, tinea captitis, tinea cruris and different ring worm infections. In some of the patients suffering with these diseases, the infection can become systemic causing fungal septicemia, or brain/meningal infection, leading to seizures and even death.

Immunocompromised patients are particularly susceptible to fungal infections. In those patients, fungal organisms may cause infections that are difficult to eradicate. Immunocompromised patients include, for example, those infected by HIV, those undergoing chemotherapy, transplant recipients, or cancer patients receiving immunosuppressive medications. Fungal organisms which attack immunocompromised patients are often called "opportunistic fungi." These may be opportunistic yeasts, such as species of Candida, Trichosporon, and Cryptococcus.

In immunocompromised patients, systemic diseases caused by different opportunistic fungal organisms can lead to frequent or prolonged hospitalization and even death. More specifically, opportunistic fungal species can cause kidney, liver, spleen, heart, eyes, brain or skin infections. Cryptococcus, for example, can cause brain (meningoencephalitis), prostate, bone or other infections. Trichosporon can infect kidneys, eyes, skin and the lungs.

In many instances, fungal species are introduced into the body iatrogenically during an invasive procedure such as a peripheral or central vascular catheter insertion. Fungal species are also introduced in unscheduled invasive procedures secondary to accidents or exposure to dirt, soil or other sources of fungal organisms. Either type of introduction may lead to fungal infections requiring medical attention and treatment.

There are several anti-fungal compounds (or medications) used to treat various types of fungi and the associated infection. Anti-fungal compounds may have fungicidal or fungistatic activity. Anti-fungal compounds, such as those discussed below, have been used to treat superficial fungal infections such as those occurring on skin or nails, as well as systemic infections such as fungal pneumonia. While effective against various fungal infections, some anti-fungal compounds may cause unwanted side effects. Other anti-fungal compounds may cause adverse drug interactions when used in combination with terfenadine (sold as Seldane® product), astemizole (sold as Hismanal® product), and Cimetidine (sold as Tagamet® product).

Amphotericin B, which is a polyene, is used to treat systemic mycoses such as Candida, Cryptococcus, Histoplasmosis, Blastomyces, Coccidioides, Fusarium, Aspergillus and Trichosporon. Amphotericin B is generally administered intravenously and requires hospitalization for treatment. Considered the "gold standard" for treatment of fungal infections, Amphotericin B is reserved for life threatening fungal infections. Amphotericin B, however, has restrictions on allowable dosages. The daily dose generally should not exceed 1.5 mg/kg. Side effects from Amphotericin B may include acute toxicity, nephrotoxicity, thrombophlebitis, and erythroid suppression. Other side effects, such as fever, shaking, chills, hypotension, nausea and vomiting, have also been observed.

Another anti-fungal compound, ketoconazole (an azole derivative), is a fungistatic agent which is effective against Trichophyton, Microsporum and Candidas. The use of ketoconazole can be associated with the gastrointestinal (GI) system distress, hepatitis, endocrine effects. Other side effects include nausea, vomiting and abdominal pain. Ketoconazole, which is administered as an oral formulation, generally needs an acidic environment to be absorbed via the gut. Consequently, no parenteral formulation of ketaconazole currently exists. Complications can develop when ketaconazole is used with other pharmaceutical compounds such as terfenadine (sold as Seldane® product), astemizole (sold as Hismanal® product), and Cimetidine (sold as Tagamet® product).

Itraconazole, another azole derivative, has similar drug interactions as ketoconazole. Patients treated with itraconazole can suffer side effects such as GI disorders, hepatitis, rash formation or hypertension. Like ketoconazole, GI absorption of itraconazole is pH dependent. No parenteral formulation exists. Itraconazole is often used to treat infections from Blastomyces, Histoplasmosis, Aspergillus and Cryptococcus.

The antifungal compound, flucytosine (a fluoropyrimidine), is effective against *Candida spp., Cryptococcus neoformans, Coccidioides immitis, Histoplasmosis capsulatum, Blastomyces dermatitidis, Aspergillus spp.* and dematiaceous fungi. Use of flucytosine is sometimes associated with high rates of accumulation of flucytosine itself in the body tissues if the patient suffers from renal impairment. Flucytosine is a fungistatic anti-fungal compound. Its side effects can include hepatitis, GI distress, diarrhea, myelosupression and rash formation.

Terbinafine (an allylamine) is used in topical applications against *Trichophyton mentagrophytes*. Terbinafine, however, can cause irritation, burning and itching.

Griseofulvin, a microtubule inhibitor, is also used to treat Trichophyton infections. Griseofulvin can cause side effects such as skin rashes, alcohol potentiation, nausea, vomiting, epigastric distress, mental confusion and impairment in performance of routine activities.

Despite the existence of known anti-fungal compounds, the pharmaceutical industry is always in search of improved anti-fungal compounds which control a broader spectrum of diseases while possessing fewer side effects, better toxicology profiles, and fewer drug interactions. As increasingly more patients, through immunosuppressant therapy or diseases, risk fungal infections, there exists a need to develop more effective anti-fungal compositions and therapies. Moreover, there exists a need to lower the required dose of anti-fungal compounds and to improve anti-fungal therapies while maintaining efficacy and thereby lowering toxicity and side effects.

SUMMARY OF THE INVENTION

In view of the pharmaceutical industry's search for improved anti-fungal compounds, the present invention offers a significant advance over current practices. The present invention relates to use of N-alkyl compounds or salts thereof to increase the efficacy and decrease the dosage of anti-fungal compounds to treat various fungal infections. The use of N-alkyl heterocyclic compounds or salts thereof, according to the invention, can thereby reduce the cost, the side effects and the toxicity profiles of current anti-fungal compounds.

Accordingly, the invention provides a method for increasing the effectiveness of an anti-fungal compound in the treatment of a fungal infection. This method administers to a mammal, preferably a human, in recognized need thereof, an anti-fungal compound and an N-alkyl heterocyclic compound or a salt thereof. The N-alkyl heterocyclic compound or salt thereof increases or potentiates the anti-fungal activity of the anti-fungal compound. The combination of the anti-fungal compound with an N-alkyl heterocyclic compound or salt thereof achieves superior anti-fungal activity at lower concentrations and lower cost than the anti-fungal compound alone. The N-alkyl heterocyclic compound has the formula:

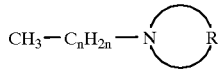

For the N-alkyl heterocyclic compound or salt thereof, n may vary from 5 to 17 and the heterocyclic ring defined by

is a substituted or unsubstituted ring having four to eight members.

Another embodiment of the invention provides a method to treat a fungal infection. This method administers to a mammal, preferably a human, in recognized need thereof, an anti-fungal compound and an N-alkyl heterocyclic compound as described above or a salt thereof. The anti-fungal compound and the N-alkyl heterocyclic compound or salt thereof are administered in a combined amount effective to treat the fungal infection.

Another embodiment of the invention provides a pharmaceutical composition. The composition contains at least one anti-fungal compound, an N-alkyl heterocyclic compound of the above formula or a salt thereof, and a pharmaceutically-acceptable carrier. In the composition, the anti-fungal compound and the N-alkyl heterocyclic compound or salt thereof are present in a combined amount effective to treat a fungal infection.

Yet another embodiment of this invention provides a method to control the growth of a fungal organism on a substrate to be inserted into the body. The method comprises the step of contacting the substrate with an anti-fungal compound and an N-alkyl heterocyclic compound or a salt thereof, described above. The anti-fungal compound and the N-alkyl heterocyclic compound or salt thereof are present in a combined amount effective to treat a fungal infection.

These and other features and advantages of the present invention will be made more apparent from the following detailed description and preferred embodiments.

DETAILED DESCRIPTION

The invention relates to a method for increasing the effectiveness of an anti-fungal compound in the treatment of a fungal infection. This method administers to a mammal, preferably a human, in recognized need thereof, an anti-fungal compound and an N-alkyl heterocyclic compound or a salt thereof.

In one embodiment, the invention relates to a method to treat a fungal infection. This method administers to a mammal, preferably a human, in recognized need thereof, an anti-fungal compound and an N-alkyl heterocyclic compound or a salt thereof. The anti-fungal and the N-alkyl heterocyclic compound or salt thereof are administered in a combined amount effective to treat a fungal infection.

In another embodiment, the invention relates to a pharmaceutical composition to treat fungal infections. The composition comprises an anti-fungal compound, an N-alkyl heterocyclic compound or a salt thereof, and a pharmaceutically acceptable carrier. The anti-fungal compound and the N-alkyl heterocyclic compound or salt thereof are present in a combined amount effective to treat a fungal infection.

According to the invention, the combination of an anti-fungal compound and an N-alkyl heterocyclic compound or a salt thereof demonstrates an unexpected, enhanced anti-fungal effect. That is, the combination of an anti-fungal compound and an N-alkyl heterocyclic compound or a salt thereof achieves superior anti-fungal activity, and generally at lower anti-fungal compound concentrations, as compared to the fungicidal or fungistatic capability of the anti-fungal compound alone. Thus, the N-alkyl heterocyclic compound or salt thereof potentiates the anti-fungal activity of the anti-fungal compound. The combination may have a fungicidal or fungistatic effect. Preferably, the combination has a fungicidal effect. Such a superior effect presents a distinct therapeutic advantage and increases an individual anti-fungal compound's effectiveness per unit dosage.

According to the invention, an N-alkyl heterocyclic compound or a salt thereof may be used to increase the effectiveness of any anti-fungal compound or a mixture of anti-fungal compounds. Preferred anti-fungal compounds include, for example, Amphotericin B, ketoconazole, miconazole, fluconazole, itraconazole, griseofulvin, flucytosine, terbinafine, naftifine and amorolfine and mixtures thereof. The N-alkyl heterocyclic compound or salt thereof, or a mixture of N-alkyl heterocyclic compounds or salts thereof, may be used with and in the same pharmaceutical formulation and treatment regimen as the particular anti-fungal compound is typically used. Preferably, one or more N-alkyl heterocyclic compounds or salts thereof are incorporated into the formulation of the anti-fungal compound. The combination of an anti-fungal compound and an N-alkyl heterocyclic compound or a salt thereof may be used to control fungal infections including, but not limited to, Cryptococcosis, Candidosis, Aspergillosis, Coccidioidomycosis, Histoplasmosis, Blastomycosis, Trichosporonosis and Trichophyton infections.

The N-alkyl heterocyclic compounds or salts thereof employed in the invention have the following general formula:

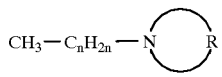

The variable "n" may vary from 5 to 17, and preferably from 9 to 15. Most preferably, n is 11. The alkyl chain defined by $CH_3-C_nH_{2n}-$ may be branched or unbranched, saturated or unsaturated. Branched alkyl chains may lose some of their solubility in water or other aqueous systems. Unbranched alkyl groups are generally preferred. The heterocyclic ring defined by

may have four to eight members and is preferably a five-, six-, seven-, or eight-membered ring. Most preferably the heterocyclic ring is a six-membered or five-membered ring.

Although the heterocyclic ring always contains one nitrogen atom, the remainder is generally a carbo cycle. However, the ring may contain one or more additional heteroatoms selected from N, O, or S. The ring may be saturated or unsaturated. The ring may also have common substituents such as alkyl groups, substituted alkyl groups (such as hydroxyalkyl), alkenyl groups, substituted alkenyl groups, amino groups, an oxo group to form a cyclic ketone, halogens, etc. The heterocyclic ring may also be part of a multiple ring structure.

The heterocycles listed below exemplify substituted or unsubstituted heterocyclic rings which may be used in the N-alkyl heterocyclic compounds utilized in preferred embodiments of the present invention. Examples of five-membered heterocyclic rings include, but are not limited to, pyrrolidinyl, 2-pyrrolidinonyl, pyrrolinyl, pyrazolidinyl, pyrazolinyl, pyrazolyl, imidazolidinyl, imidazolinyl, imidazolyl and oxazolidinyl. Six-membered rings include, but are not limited to, piperidinyl, piperazinyl, and morpholinyl. Seven- and eight-membered rings such as hexamethyleneiminyl and heptamethyleneiminyl may also be used in the present invention. One of ordinary skill will appreciate that other heterocyclic rings may also be used.

N-alkyl heterocyclic compounds useful in the invention are available either commercially from chemical supply houses or may be prepared from starting materials using well-known literature methods. U.S. Pat. No. 5,250,194 discloses exemplary methods and is incorporated herein by reference. U.S. Pat. No. 5,250,194 also describes N-dodecyl heterocyclic compounds and their use as anti-fungal compounds for aqueous systems to inhibit the growth of microorganisms, the formation of slime in aqueous systems, or the disfigurement or deterioration of substances susceptible to microbiological growth. One example of an N-alkyl heterocyclic compound useful as such an anti-fungal compound is N-dodecyl morpholine (DDM). DDM is manufactured by BASF GmbH and by Buckman Laboratories International Inc., Memphis, Tenn.

Preferred N-alkyl heterocyclic compounds for use in the present invention include N-dodecyl morpholine, N-dodecyl imidazole, N-dodecyl-2,6-dimethyl-morpholine, N-dodecyl-5-chloromethyl-2-oxazolidinone, N-dodecyl-2-pyrrolidinone, N-dodecyl hexamethyleneimine, N-dodecyl pyrrolidine, N-dodecyl-3-methyl-piperidine, N-dodecyl piperidine, N-dodecyl-4-methyl-piperidine and N-dodecyl-2-methyl-piperidine. Most preferred of these compounds are N-dodecyl morpholine, (DDM), and N-dodecyl imidazole, (DDI).

Salts of N-alkyl heterocyclic compounds, including those described above, may also be used in the present invention. Such salts are formed at the nitrogen moiety of the N-alkyl heterocyclic compound (hereafter referred to as "quaternized N-alkyl heterocyclic salts") and have the general formula

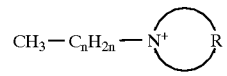

where n and

are as defined above.

As discussed above, the combination, according to the invention, of an anti-fungal compound and an N-alkyl heterocyclic compound or a salt thereof may be used in the same manner and under the same treatment regimen as for the anti-fungal compound alone. Preferably, the N-alkyl heterocyclic compound or salt thereof is administered together with, and more preferably in the same pharmaceutical composition as, the anti-fungal compound. A pharmaceutical composition of the invention comprises the combination with a pharmaceutically or physiologically acceptable carrier. If appropriate, either the anti-fungal compound or the N-alkyl heterocyclic compound or salt thereof may be administered in the form of a physiologically acceptable salt, for example, an acid-addition salt. The combination, according to the invention, can be administered orally, topically, rectally, anterally, internally, by boluses, or parenterally.

Suitable solid or liquid formulations include, for example, granules, powders, tablets, microcapsules, suppositories, syrups, elixirs, suspensions, emulsions, aerosols, drops or injectable solutions. Also, the combination of an anti-fungal compound and an N-alkyl heterocyclic compound or a salt thereof of the invention may be employed in protracted release preparations. Commonly used additives in pharmaceutical compositions include, but are not limited to, excipients, disintegraters, binders, coating agents, swelling agents, glidants, or lubricants, flavors, sweeteners or solubilizers. More specifically, frequently used additives are, for example, magnesium stearate, magnesium carbonate, titanium dioxide, lactose, mannitol and other sugars, talc, lactalbumin, gelatin, corn starch, cellulose and its derivatives, animal and vegetable oils, polyethylene glycols and solvents. Common solvents include sterile water, buffered water, and monohydric or polyhydric alcohols such as glycerol or propylene glycol.

The pharmaceutical compositions are preferably produced and administered in dosage units, each unit containing an effective amount of an anti-fungal compound and an N-alkyl heterocyclic compound or a salt thereof or a corresponding physiologically acceptable salt of the anti-fungal compound and/or the N-alkyl heterocyclic compound. The effective amount to treat a fungal infection may range from about 1 to 500 mg/kg of body weight per day for the anti-fungal compound and the N-alkyl heterocyclic compound or salt thereof. In general, an effective dosage amount used on a patient ranges from 1 to 5 mg daily for Amphotericin B to 50 to 150 mg/kg/day for flucytosine. Dosages for ketoconazole are 200 mg/day and for itraconazole, 200 mg/day ( 400 mg/day if no improvement seen). Griseofulvin is administered in three daily doses of 250 mg each. In a preferred embodiment, combinations of an anti-fungal compound and an N-alkyl heterocyclic compound are those combinations having a weight ratio of anti-fungal compound to N-alkyl heterocyclic compound from about 99:1 to about 1:99. The weight ratio may vary depending on the anti-fungal compound, the intended treatment, and the fungal organism encountered.

The combination of an anti-fungal compound and an N-alkyl heterocyclic compound or a salt thereof according to the invention may also be used to control the growth of fungal organisms on various substrates inserted into the body such as prosthetics or catheters. The method comprises the step of contacting the substrate with an anti-fungal compound and an N-alkyl heterocyclic compound or a salt thereof, as described above. The step of contacting may apply, coat or impregnate the combination of an anti-fungal compound and an N-alkyl heterocyclic compound or a salt thereof onto or into the surface of the substrate to be inserted into the body. The anti-fungal compound and N-alkyl heterocyclic compound or salt thereof are present in a combined amount effective to control the growth of at least one fungal organism on the substrate and reduce or prevent fungal infection of the surrounding bodily tissue. Preferably, the method may be used to eliminate or prevent substantially all fungal growth on the substrate.

The following examples are intended to illustrate, not limit, the present invention.

EXAMPLES:

One procedure for determining a potentiating interaction between two compounds utilizes the same technique and apparatus as that used in the basic determination of antifungal activity for a single compound. However, the identification of an interaction between two compounds requires a special arrangement of treatments in an experimental design known as a "factorial" arrangement. This is commonly accomplished using a "checkerboard" design in which each vertical column represents a different concentration of Compound A, and each horizontal row represents a different concentration of Compound B. The concentration series for each compound alone begins at "zero". Thus, the correct factorial design provides:

(a) a "no chemical" control (position row 1, column 1), (b) results for the concentration series of each chemical alone (on row 1: chemical B=0, thus chemical A is in a series by itself; on column 1, compound A=0, thus compound B is in a series by itself), and (c) each concentration of compound A in a combination with each concentration of compound B.

In the procedure, each position in the factorial or checkerboard design is occupied by a culture tube containing 5 ml of sterile liquid culture medium. Individual stock solutions for both compounds are prepared, and the appropriate volume ($\mu$l) is added to the medium to achieve the required concentration specified by the test protocol. Each tube is inoculated with 100 $\mu$l of spore suspension prepared from the test fungus (*Aspergillus niger* or *Candida Albicans*). The suspension is prepared by swabbing the surface of a viable culture (agar slant) and introducing the collected spores into a bottle containing 100 ml of sterile water. The spore suspension is complete when the optical density=0.28 at 686 nm. The inoculated treatments are incubated in the dark at 28° C. for seven days. All tubes then are observed for either the presence or absence of fungal mat growing on the surface of the liquid medium.

The key items of data recorded are:

(1) the lowest concentration (minimum inhibitory concentration, MIC) of each test compound separately for which there was no growth, and/or (2) the lowest concentration of compound A in combination with compound B for which there was no growth.

The above procedure was used to determine the potentiating effect of an N-alkyl heterocyclic compound or a salt thereof with various anti-fungal compounds. Tables 1–4 show the results of the various tests and the potentiation of an anti-flmgal effect using BUSAN® 2180 product available from Buckman Laboratories Incorporated, Memphis, Tenn. BUSAN® 2180 product is a 60% by weight formulation of the N-alkyl heterocyclic compound dodecyl-morpholine (DDM). Tables 1–4 below present the lowest concentrations of each test compound separately for which there was no growth and/or the lowest concentration of compound A in combination with compound B for which there was no growth. A plus (+) sign represents the growth and a minus (–) sign represents the absence of fungal growth. For Tables 1–3:

Ketoconazole or Miconazole were combined at dosages of 0 to 50 ppm active ingredient (a.i.) by increments of 5 ppm a.i. with BUSAN® 2180 of 0 to 100 ppm DDM a.i. by increments of 10 ppm a.i. against *Aspergillus niger* and *Candida albicans*. The medium of growth used was Nutrient Salts Broth without addition of yeast extract.

TABLE 1

Treatments incolated with *A. Niger*

| ppm a.i. | | Ketoconazole | | | | | | | | | |
|---|---|---|---|---|---|---|---|---|---|---|---|
| | | 0 | 5 | 10 | 15 | 20 | 25 | 30 | 35 | 40 | 45 | 50 |
| BUSAN® 2180* | 0 | + | + | + | + | + | + | + | + | + | + | + |
| | 10 | + | + | + | + | + | + | + | + | + | + | + |
| | 20 | + | + | + | + | + | + | + | + | + | + | + |
| | 30 | + | + | + | + | + | + | + | + | + | + | + |
| | 40 | + | + | + | + | + | + | + | + | + | + | + |
| | 50 | + | + | + | + | – | – | – | – | – | – | – |
| | 60 | + | + | – | – | – | – | – | – | – | – | – |
| | 70 | – | – | – | – | – | – | – | – | – | – | – |
| | 80 | – | – | – | – | – | – | – | – | – | – | – |
| | 90 | – | – | – | – | – | – | – | – | – | – | – |
| | 100 | – | – | – | – | – | – | – | – | – | – | – |

*BUSAN ® 2180: 60% DDM (a.i.), 10% propylene glycol, 20% Emulsifiers, 10% Water

TABLE 2

Treatments incolated with *C. albicans*

| ppm a.i. | | Ketoconazole | | | | | | | | | |
|---|---|---|---|---|---|---|---|---|---|---|---|
| | | 0 | 5 | 10 | 15 | 20 | 25 | 30 | 35 | 40 | 45 | 50 |
| BUSAN® 2180* | 0 | + | + | + | + | + | + | + | + | + | + | + |
| | 10 | + | – | – | – | – | – | – | – | – | – | – |
| | 20 | – | – | – | – | – | – | – | – | – | – | – |
| | 30 | – | – | – | – | – | – | – | – | – | – | – |
| | 40 | – | – | – | – | – | – | – | – | – | – | – |
| | 50 | – | – | – | – | – | – | – | – | – | – | – |
| | 70 | – | – | – | – | – | – | – | – | – | – | – |
| | 80 | – | – | – | – | – | – | – | – | – | – | – |
| | 90 | – | – | – | – | – | – | – | – | – | – | – |
| | 100 | – | – | – | – | – | – | – | – | – | – | – |

*BUSAN ® 2180: 60% DDM (a.i.), 10% propylene glycol, 20% Emulsifiers, 10% Water

TABLE 3

Treatments incolated with *C. albicans*

| ppm a.i. | | Miconazole | | | | | | | | | |
|---|---|---|---|---|---|---|---|---|---|---|---|
| | | 0 | 5 | 10 | 15 | 20 | 25 | 30 | 35 | 40 | 45 | 50 |
| BUSAN® 2180* | 0 | + | + | – | – | – | – | – | – | – | – | – |
| | 10 | + | – | – | – | – | – | – | – | – | – | – |
| | 20 | – | – | – | – | – | – | – | – | – | – | – |
| | 30 | – | – | – | – | – | – | – | – | – | – | – |
| | 40 | – | – | – | – | – | – | – | – | – | – | – |
| | 50 | – | – | – | – | – | – | – | – | – | – | – |
| | 60 | – | – | – | – | – | – | – | – | – | – | – |
| | 70 | – | – | – | – | – | – | – | – | – | – | – |
| | 80 | – | – | – | – | – | – | – | – | – | – | – |
| | 90 | – | – | – | – | – | – | – | – | – | – | – |
| | 100 | – | – | – | – | – | – | – | – | – | – | – |

*BUSAN ® 2180: 60% DDM (a.i.), 10% propylene glycol, 20% Emulsifiers, 10% Water

For Table 4:

Miconazole was combined at dosages of 0 to 20 ppm a.i. by increments of 2 ppm a.i. with BUSAN® 2180 of 0 to 100 ppm DDM a.i. by increments of 10 ppm a.i. against *Aspergillus niger* and *Candida albicans*. The medium of growth used was Nutrient Salts Broth without addition of yeast extract.

TABLE 4

Treatments incolated with *A. Niger*

| ppm a.i. | | Miconazole | | | | | | | | | |
|---|---|---|---|---|---|---|---|---|---|---|---|
| | | 0 | 2 | 4 | 6 | 8 | 10 | 12 | 14 | 16 | 18 | 20 |
| BUSAN® 2180* | 0 | + | + | + | + | + | + | + | + | + | + | + |
| | 10 | + | + | + | + | + | + | + | + | + | + | + |
| | 20 | + | + | + | + | + | + | + | – | – | – | – |
| | 30 | + | + | + | + | – | – | – | – | – | – | – |
| | 40 | + | + | + | + | – | – | – | – | – | – | – |
| | 50 | + | + | – | – | – | – | – | – | – | – | – |
| | 60 | + | – | – | – | – | – | – | – | – | – | – |
| | 70 | – | – | – | – | – | – | – | – | – | – | – |
| | 80 | – | – | – | – | – | – | – | – | – | – | – |
| | 90 | – | – | – | – | – | – | – | – | – | – | – |
| | 100 | – | – | – | – | – | – | – | – | – | – | – |

*BUSAN ® 2180: 60% DDM (a.i.), 10% propylene glycol, 20% Emulsifiers, 10% Water

The claimed invention is:

1. A method for increasing the effectiveness of an anti-fungal compound used to treat a fungal infection comprising the step of administering to a mamnmal, in recognized need thereof, the anti-fungal compound and an N-alkyl heterocyclic compound or a salt thereof, wherein the N-alkyl heterocyclic compound is of the formula:

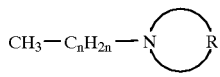

where "n" varies from 5 to 17 and the heterocyclic ring defined by

is a substituted or unsubstituted ring having four to eight members, and wherein the anti-fungal compound and the N-alkyl heterocyclic compound or the salt thereof are administered in a combined amount effective to treat the fungal infection and the N-alkyl heterocyclic compound or the salt thereof is present in an amount effective to potentiate the anti-fungal activity of the anti-fungal compound.

2. A method of claim 1, wherein n varies from 9 to 15, and the heterocyclic ring is selected from the group consisting of pyrrolidinyl, 2-pyrrolidinonyl, pyrrolinyl, pyrazolidinyl, pyrazolinyl, pyrazolyl, imidazolidinyl, imidazolinyl, imidazolyl, oxazolidinyl, piperidinyl, piperazinyl, morpholinyl, hexamethyleneiminyl, and heptamethylene-iminyl.

3. A method of claim 1, wherein the anti-fungal compound is selected from the group consisting of Amphotericin B, ketoconazole, miconazole, fluconazole, itraconazole, griseofulvin, flucytosine, terbinafine, naftifine and amorolf-ine and mixtures thereof, and the N-alkyl heterocyclic compound is selected from the group consisting of: N-dodecyl morpholine, N-dodecyl imidazole, N-dodecyl-2,6-dimethyl-morpholine, N-dodecyl-5-chloromethyl-2-oxazolidinone, N-dodecyl-2-pyrrolidinone, N-dodecyl hexamethyleneimine, N-dodecyl pyrrolidine, N-dodecyl-3-methyl-piperidine, N-dodecyl piperidine, N-dodecyl-4-methyl-piperidine and N-dodecyl-2-methyl-piperidine.

4. A method of claim 3, wherein the N-alkyl heterocycle is N-dodecyl morpholine.

5. A method of claim 3, wherein the N-alkyl heterocycle is N-dodecyl imidazole.

6. A method to treat a fungal infection comprising the step of administering to a mammal, in recognized need thereof, an anti-fungal compound and an N-alkyl heterocyclic compound or a salt thereof, where the N-alkyl heterocyclic compound is of the formula:

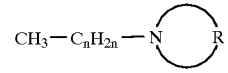

where "n" varies from 5 to 17 and the heterocyclic ring defined by

is a substituted or unsubstituted ring having four to eight members, and wherein the anti-fungal compound and the N-alkyl heterocyclic compound or the salt thereof are administered in a combined amount effective to treat the fungal infection, and the N-alkyl heterocyclic compound or the salt thereof is present in an amount effective to potentiate the anti-fungal activity of the anti-fiungal compound.

7. A method of claim 6, wherein n varies from 9 to 15, and the heterocyclic ring is selected from the group consisting of pyrrolidinyl, 2-pyrrolidinonyl, pyrrolinyl, pyrazolidinyl, pyrazolinyl, pyrazolyl, imidazolidinyl, imidazolinyl, imidazolyl, oxazolidinyl, piperidinyl, piperazinyl, morpholinyl, hexamethyleneiminyl, and heptamethylene-iminyl.

8. A method of claim 6, wherein the anti-fungal compound is selected from the group consisting of Amphotericin B, ketoconazole, miconazole, fluconazole, itraconazole, griseofulvin, flucytosine, terbinafine, naftifine and amorolf-ine and mixtures thereof, and the N-alkyl heterocyclic compound is selected from the group consisting of N-dodecyl morpholine, N-dodecyl imidazole, N-dodecyl-2, 6-dimethyl-morpholine, N-dodecyl-5-chloromethyl-2-oxazolidinone, N-dodecyl-2-pyrrolidinone, N-dodecyl hexamethyleneimine, N-dodecyl pyrrolidine, N-dodecyl-3-methyl-piperidine, N-dodecyl piperidine, N-dodecyl-4-methyl-piperidine and N-dodecyl-2-methyl-piperidine.

9. A method of claim 8, wherein the N-alkyl heterocycle is N-dodecyl morpholine.

10. A method of claim 8, wherein the N-alkyl heterocycle is N-dodecyl imidazole.

11. A pharmaceutical composition comprising an anti-fungal compound, an N-alkyl heterocyclic compound or a salt thereof, and a pharmaceutically-acceptable carrier, where the N-alkyl heterocyclic compound is of the formula:

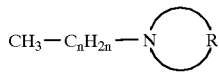

where "n" varies from 5 to 17 and the heterocyclic ring defined by

is a substituted or unsubstituted ring having four to eight members, and wherein the anti-fungal compound and the N-alkyl heterocyclic compound or the salt thereof are present in a combined amount effective to treat the fungal infection, and wherein the N-alkyl heterocyclic compound or the salt thereof is present in an amount effective to potentiate the anti-fungal activity of the anti-fiungal compound.

12. A pharmaceutical composition of claim 11, wherein the anti-fungal compound is selected from the group consisting of Amphotericin B, ketoconazole, miconazole, fluconazole, itraconazole, griseofulvin, flucytosine, terbinafine, naftifine and amorolfine and mixtures thereof, and the N-alkyl heterocyclic compound is selected from the group consisting of: N-dodecyl morpholine, N-dodecyl imidazole, N-dodecyl-2,6-dimethyl-morpholine, N-dodecyl-5-chloromethyl-2-oxazolidinone, N-dodecyl-2-pyrrolidinone, N-dodecyl hexamethyleneimine, N-dodecyl pyrrolidine, N-dodecyl-3-methyl-piperidine, N-dodecyl piperidine, N-dodecyl-4-methyl-piperidine and N-dodecyl-2-methyl-piperidine.

13. A pharmaceutical composition of claim 12, wherein the N-alkyl heterocycle is N-dodecyl morpholine or N-dodecyl imidazole.

14. A pharmaceutical composition of claim 12, wherein the composition is an aerosol formulation.

15. A pharmaceutical composition of claim 11, wherein n varies from 9 to 15, and the heterocyclic ring is selected from the group consisting of pyrrolidinyl, 2-pyrrolidinonyl, pyrrolinyl, pyrazolidinyl, pyrazolinyl, pyrazolyl, imidazolidinyl, imidazolinyl, imidazolyl, oxazolidinyl, piperidinyl, piperazinyl, morpholinyl, hexamethyleneiminyl, and heptamethyleneiminyl.

16. A method to control the growth of a fungal organism on a substrate to be inserted into the body, the method comprising the step of contacting the substrate with an anti-fungal compound and an N-alkyl heterocyclic compound or a salt thereof, where the N-alkyl heterocyclic compound is of the formula:

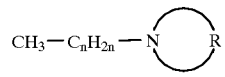

where "n" varies from 5 to 17 and the heterocyclic ring defined by

is a substituted or unsubstituted ring having four to eight members, and wherein the anti-fungal compound and the N-alkyl heterocyclic compound or the salt thereof are present in a combined amount effective to treat the fungal infection, and wherein the N-alkyl heterocyclic compound or the salt thereof is present in an amount effctive to plotentiate the anti-fingal activity of the anti-fungal compound.

17. A method of claim 16, wherein n varies from 9 to 15, and the heterocyclic ring is selected from the group consisting of pyrrolidinyl, 2-pyrrolidinonyl, pyrrolinyl, pyrazolidinyl, pyrazolinyl, pyrazolyl, imidazolidinyl, imidazolinyl, imidazolyl, oxazolidinyl, piperidinyl, piperazinyl, morpholinyl, hexamethyleneiminyl, and heptamethyleneiminyl.

18. A method of claim 16, wherein the anti-fungal compound is selected from the group consisting of Amphotericin B, ketoconazole, miconazole, fluconazole, itraconazole, griseofulvin, flucytosine, terbinafine, naftifine and amorolfine and mixtures thereof, and the N-alkyl heterocyclic compound is selected from the group consisting of: N-dodecyl morpholine, N-dodecyl imidazole, N-dodecyl-2,6-dimethyl-morpholine, N-dodecyl-5-chloromethyl-2-oxazolidinone, N-dodecyl-2-pyrrolidinone, N-dodecyl hexamethyleneimine, N-dodecyl pyrrolidine, N-dodecyl-3-methyl-piperidine, N-dodecyl piperidine, N-dodecyl-4-methyl-piperidine and N-dodecyl-2-methyl-piperidine.

19. A method of claim 18, wherein the N-alkyl heterocycle is N-dodecyl morpholine.

20. A method of claim 18, wherein the N-alkyl heterocycle is N-dodecyl imidazole.

* * * * *

UNITED STATES PATENT AND TRADEMARK OFFICE
CERTIFICATE OF CORRECTION

PATENT NO. : 5,925,616
DATED : July 20, 1999
INVENTOR(S) : Marilyn S. Whittemore It is certified that error appears in the above-identified patent and that said Letters Patent is hereby corrected as shown below:

Title,
Change "H-ALKYL" to -- N-ALKYL --.

CLAIMS,

Column 9,
Line 49, change "mamnmal" to -- mammal --.

Column 10,
Line 53, change "anti-fiungal" to -- anti-fungal --.

Column 11,
Line 33, change "anti-fiungal" to -- anti-fungal --.

Column 12,
Line 29, change "effctive" to -- effective --.
Line 30, change "plotentiate" to -- potentiate -- and change anti-fiungal" to -- anti-fungal --.

Signed and Sealed this

Twenty-fifth Day of September, 2001

Attest:

NICHOLAS P. GODICI
Attesting Officer    Acting Director of the United States Patent and Trademark Office